United States Patent
Wang et al.

(10) Patent No.: US 6,197,319 B1
(45) Date of Patent: *Mar. 6, 2001

(54) COSMETIC COMPOSITIONS CONTAINING POLYSACCHARIDE/PROTEIN COMPLEXES

(75) Inventors: Tian Xiang Wang, Edison; Debra Marsha Verdon DiGirolamo, Holmdel; Julio Gans Russ, Westfield, all of NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/456,575

(22) Filed: Dec. 8, 1999

Related U.S. Application Data

(63) Continuation of application No. 09/175,942, filed on Oct. 21, 1998.
(51) Int. Cl.⁷ .............................. A61K 6/00; A61K 7/00
(52) U.S. Cl. ................. 424/401; 424/70.1; 424/70.13; 424/70.14; 424/70.19; 424/70.27; 424/70.28; 424/74; 424/59; 424/63; 514/844; 514/845; 514/846; 514/847

(58) Field of Search ................... 424/401, 70.1, 424/70.4, 70.22, 70.23, 70.24, 70.27, 74, 70.13, 70.14, 70.19, 70.28, 59, 63; 514/844, 845, 846, 847

(56) References Cited

U.S. PATENT DOCUMENTS

| | | | |
|---|---|---|---|
| 5,597,386 | * | 1/1997 | Igarashi et al. ................... 8/405 |
| 5,700,397 | * | 12/1997 | Maeda et al. ..................... 252/312 |
| 5,700,455 | * | 12/1997 | Hinterwaldner et al. ......... 424/70.14 |
| 6,042,815 | * | 3/2000 | Kellner et al. ...................... 424/63 |

* cited by examiner

Primary Examiner—Thurman K. Page
Assistant Examiner—Liliana Di Nola-Baron
(74) Attorney, Agent, or Firm—Julie Blackburn

(57) ABSTRACT

In an emulsion cosmetic composition for application to skin containing water and at least one surfactant, the improvement wherein the composition also contains a water soluble, protein polysaccharide complex ("PPC") having a net positive or negative charge, which is the reaction product of at least one protein and at least one anionic polysaccharide.

17 Claims, No Drawings

COSMETIC COMPOSITIONS CONTAINING POLYSACCHARIDE/PROTEIN COMPLEXES

This is a continuation of abandoned application Ser. No. 09/175,942, filed Oct. 21, 1998.

TECHNICAL FIELD

The invention is in the field of cosmetic composition for application to the skin.

BACKGROUND OF THE INVENTION

The use of polysaccharides and proteins in cosmetic compositions is well known in the art. Polysaccharides are known to be good humectanits, film formers, and function as skin moisturizers. Certain polysaccharides also have gelling ability and are useful in formation of higher viscosity liquid or solid, compositions. However, polysaccharides may tend to provide a heavy, sticky feel on the skin and, when used in quantities sufficient to cause gelling, may provide products which are not aesthetically pleasing. Proteins are naturally occuring long-chain, high molecular weight polymers formed by the self-condensation of amino acids. Proteins are excellent film formers, conditioning agents, and moisturizers for hair and skin. However, natural proteins generally have limited use in cosmetics and toiletries because they are somewhat unstable and tend to precipitate or denature when exposed to high temperatures or salt solutions. In addition they are easily hydrolyzed by chemical reagents or acids and bases. Even if these difficulties are overcome the formulation of cosmetic products containing proteins is further fraught with difficulty since each protein has an isoelectric point i.e. a pH at which the protein is neutral. If it is desired to form compositions having a pH which is below the isoelectric point of the protein, the protein may possibly form an insoluble precipitate if it is used in any appreciable amount.

Thus, there is a desire to formulate cosmetic compositions for application to skin or hair which provide the benefits of proteins (film forming, moisturization, and improving cosmetic appearance) and polysaccharides (humectant, film forming, and gelling ability), but without the drawbacks of each ingredient used separately.

It is an object of the invention to prepare a protein/polysaccharide complex ("PPC") which is the reaction product of at least one protein and at least one anionic polysaccharide, wherein the resulting PPC has a net charge which may be positive or negative, preferably negative.

It is an object of the invention to prepare a PPC which acts a gellant or viscosity modifier in aqueous based compositions.

It is an object of the invention to formulate a stable cosmetic compositions having a pH which is below the isoelectric point of the protein used to make the PPC.

It is an object of the invention to provide a method for forming a PPC having a net positive or negative charge (which makes the PPC water soluble).

It is an object of the invention to formulate cosmetic foundation makeup, and color cosmetic compositions which moisturize, color, and beautify the skin.

It is an object of the invention to formulate hair care products which cleanse, condition, and beautify hair.

SUMMARY OF THE INVENTION

In an emulsion cosmetic composition for application to skin or hair containing water and at least one surfactant, the improvement wherein the composition also contains a compound which is a water soluble protein polysaccharide complex ("PPC") having a net positive or negative charge, which is the reaction product of at least one protein and at least one anionic polysaccharide.

DETAILED DESCRIPTION

The compositions of the invention are in the emulsion form, i.e. water-in-oil or oil-in-water emulsion. Preferably the compositions are in the oil-in-water emulsion form.

All percentages mentioned herein are percentages by weight unless otherwise indicated.

The PPC used in the compositions of the invention are formed by the reaction of a protein and an anionic polysaccharide containing a sufficient number of pendant hydrophilic groups such that the polysaccharide has a net positive or negative charge density, preferably a net negative charge density. The net charge of the PPC will depend upon the ratio of protein to polysaccharide in the PPC and the pH at which the PPC is made. For example, if the PPC is made at a pH which is above the isoelectric point of the protein, it will have a negative charge regardless of the ratio of protein to polysaccharide. On the other hand, if it is made at a pH which is below the isoelectric point of the protein, the pH of the PPC may be positively charged if the total positive charge from the protein is more than the negative charge polysaccharide. The protein used must contain a sufficient number of amino and/or carboxyl groups such that it is capable of reacting with the hydrophilic groups on the anionic polysaccharide to form a PPC. Preferably the pendant hydrophilic groups of the polysaccharide react with amino and/or carboxyl groups of the protein via formation of ionic bonds or electrostatic interaction.

PROTEINS

A variety of proteins are suitable to make the PPC. The term "protein" when used in accordance with this invention means a peptide chain having at least two amino acid residues, preferably at least five, and more preferably more than one hundred amino acid residues. Most preferably the protein is a high molecular weight polypeptide which is preferably water soluble, and may be natural, plant (vegetable) proteins, or animal derived proteins, as well as synthetic proteins provided they react with the hydrophilic pendant groups on the polysaccharide to form a PPC. The isoelectric point of the protein used to make the PPC is not critical. Examples of natural proteins include albumen, amylase, amyloglucosidase, arginine/lysine polypeptide, casein, catalase, collagen, crystalline, cytochrome C, deoxyribonuclease, elastin, fibronectin, gelatin, gliadin, glucose oxidase, glycoproteins, hexyldecyl ester of hydrolyzed collagen, human placental protein, human placental enzymes, iodized corn protein, keratin, lactoferrin, lactoglobulin, lactoperoxidase, lipase, milk protein, hyristoyl glycine/histidine/lysin polypeptide, nisin, oxido reductase, pancreatin, papin, pepsin, placental protein, protease, saccharomyces polypeptides, serum albumin, serum protein, silk, sodium stearoyl lactalbumin, soluble proteoglycan, soybean palmitate, soy, egg, peanut, cottonseed, sunflower, pea, whey, fish, seafood, subtilisin, superoxide dismutase, sutilains, sweet almond protein, urease, wheat germ protein, wheat protein, whey protein, zein, hydrolyzed vegetable protein, and the like. Preferred is casein which is a mixture of phosphoproteins obtained from cow's milk; and milk protein which is a mixture of proteins obtained from cow's milk.

Synthetic proteins or polypeptides may also be suitable. Synthetic proteins may be made by solid phase synthesis, or via recombinant biotechnology proccesses.

POLYSACCHARIDES

A variety of anionic polysaccharides are suitable for use in making the PPC used in the compositions of the invention, provided the anionic polysaccharide contains a sufficient number of pendant hydrophilic groups to cause the resulting PPC to exhibit a net positive or negative charge. In addition, the anionic polysaccharide must be capable of reacting with the protein to form a PPC having a protein/polysaccharide ratio of about 100 to 1: to 1:100. Suitable pendant hydrophilic groups include groups, i.e. a group containing the moiety $—SO_3^-$; $—SO_4^-$; or $—OSO_2O—$; phosphate, pyruvate, and the like. The term "polysaccharide" when used in accordance with the invention means a water soluble anionic polysaccharide which (i) contains at least five saccharide moieties; and (ii) which, upon mixing with water in a ratio of about 1 to 1 at room temperature (25° C.) is capable of forming either a soft gel having a gel having a viscosity of about 1,000 to 800,000 centipoise at 25° C., and/or a gel strength of about 10 to 5,000 grams/cm² at 25° C. as measured using a TA.XT2i texture analyzer with a ½ inch diameter cylindrical probe. The term "saccharide moiety" means a polyhydroxy aldehyde or ketone, or acid hydrolysis product thereof, which, preferably, has the general formula $C_x(H_2O)_y$. Examples of saccharide moieties include the D and L forms of glucose, fructose, xylose, arabinose, fucose, galactose, pyruvic acid, succinic acid, acetic acid, galactose, 3,6-anhydrogalactose sulfate, galactose-4-sulfate, galactose-2-sulfate, galactose-2,6-disulfate, mannose, glucuronic acid, mannuronic acid, guluronic acid, galactouronic acid, rhamnose, and so on. Preferably the anionic polysaccharides used to make the PPC have molecular weights ranging from about 500 to 15,000,000 daltons, preferably 5,000 to 1,000,000, more preferably 25,000 to 500,000 daltons.

Examples of suitable anionic polysaccharides include galactans, galactomannans, glucomannans, polyuronic acids, and the like, which exhibit the requisite number of pendant hydrophilic groups, which are preferably sulfate. Suitable galactans are agar, agarose, kappa carageenan, iota carageenan, lambda carageenan, and the like. Examples of suitable galactomannans are locust bean gum and guar; examples of glucans are cellulose and derivatives thereof, starch and derivatives, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on. Also suitable are dextran sulfate, heparin, pectin, sodium alginate, and mixtures thereof.

Preferred are galactans, particularly galactans where the pendant hydrophilic groups are sulfate groups. Most preferred is agar and carageenan, which are anionic polysaccharides comprised of basic repeating units of 1,3-linked beta-D-galactopyranose and 1,4-linked 3,6-anhydro-alpha-L-galactopyranose saccharide moieties and having pendant sulfate groups. These galactans may be further modified as taught in Aoki, T. T.; Araki & M. Kitamikado; 1990, Vibrio sp. AP-2. *Eur. J. Biochem*, 187, 461–465, which is hereby incorporated by reference, provided it contains the requisite number of hydrophilic pendant groups. The average molecular weight of agar ranges between 35,700 and 144,000 daltons. The galactans suitable for use in the compositions of the invention may be from any suitable source or locale. For example an article authored by M. Lahaye and C. Rochas, *Hydrobiologia*, 221, 137–148, 1991, which is hereby incorporated by reference, discusses the numerous different types of galactans from different origins of seaweed species, all of which are suitable for use in the compositions of the invention. Also suitable for use in the compositions of the invention are chemically modified galactans, such as those taught in an article authored by K. B. Guiseley in *Industrial Polysaccharides;Genetic Engineering, Structure/Property Relations and Applications*, Edited by M. Yalpani, 1987, Elsevier Science Publishers, which is hereby incorporated by reference. The Guiseley article teaches methods for the chemical modification of agar to obtain optimum gelling properties. In general, any modification of the galactans which does not affect the helical conformation (i.e. which is obtained via linkage of the O6 and O4 of galactose to the O2 of 3,6-anhydrogalactose) will preserve the gelling capability and is suitable for use in the compositions of the invention provided the requisite number of hydrophilic groups are present. The hydrophilic groups provide a polysaccharide which is water soluble.

THE PPC

Generally, the amino and/or hydroxyl or carboxyl groups found on the protein will react with the pendant hydrophilic groups on the anionic polysaccharide to form a complex, either alone or in the presence of metal ions such as calcium, sodium, magnesium, iron, potassium, and the like, depending on the pH at which the complexation reaction is conducted. For example, if the complexation reaction is conducted above the isoelectric point of the protein used to make the PPC, it is preferable to use a metal ion to facilitate the complexation reaction. On the other hand, if the reaction is conducted at a pH which is ar the isoelectric point of the protein used to make the PPC, a metal ion may be desired to facilitate complexation, but is not necessary. Typical reactions are as set forth below:

Complexation Reaction Conducted at pH Above the Isoelectric Point of the Protein Protein

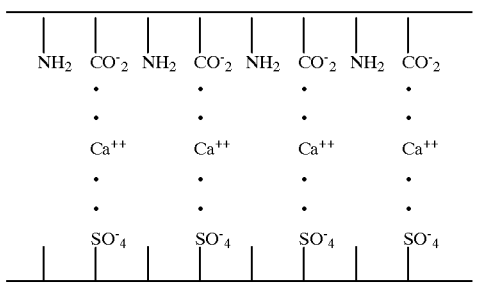

Polysaccharide with Pendant Sulfate Groups

With a typical reaction being:

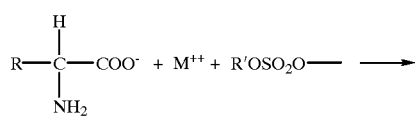

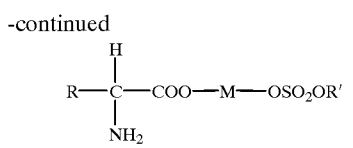

Complexation Reaction Conducted a pH Near the Isoelectric Point of Protein
Protein

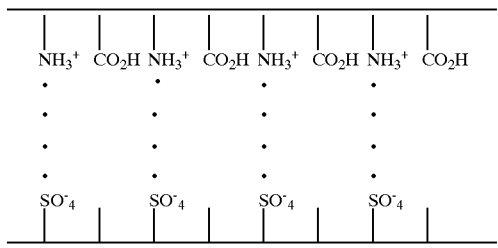

Polysaccharide with Pendant Sulfate Groups
With typical reactions being:

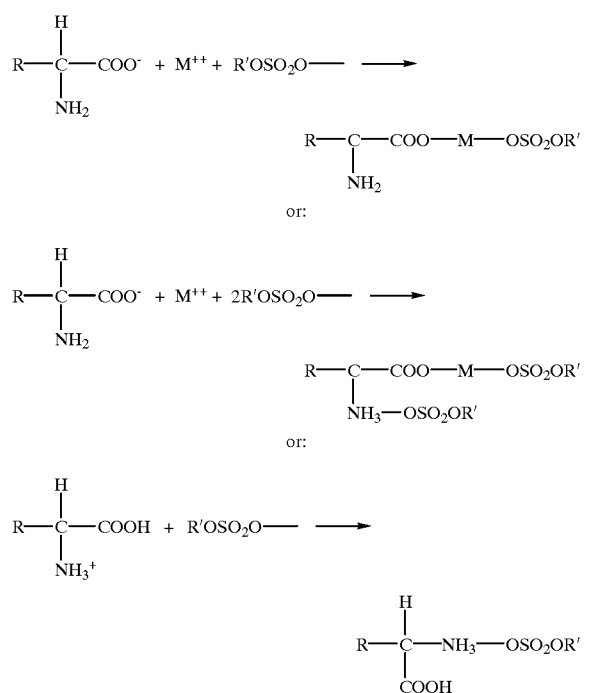

Preferably, the ratio of protein to polysaccharide in the PPC is 1:100 to 100:1, more preferably 1:50 to 50:1, most preferably 1:25 to 25:1. Preferably the PPC must contain a net negative charge. For example, when the protein having a net positive charge is reacted with the anionic polysaccharide having a net negative charge, the net negative charge of the polysaccharide is greater than the net positive charge of the protein, thus resulting in a PPC which has a net negative charge. A negative or positive charge will ensure that the PPC is water soluble, or at the very least optimally dispersible in water.

The PPC is made by combining appropriate amounts of the protein and polysaccharide in water at temperatures ranging from 25 to 90° C. Some PPC's may form at room temperature depending on the protein and polysaccharide chosen to make the PPC. Suitable ratios are 100 to 1 parts of protein to 1 to 100 parts polysaccharide. Preferably, the protein/polysaccharide complexation reaction should be conducted at a pH which is greater than the isoelectric point of the protein used to make the PPC. If more than one protein is used to make the PPC, it is recommended that the pH be equal to or greater than one or more of the proteins used. Generally, when the complexation reaction is conducted at a pH which is below the isoelectric point of the protein, it is not necessary to add metal ions. However, at this pH, the PPC may form a water insoluble precipitate (also referred to as an M-complex) if the ratio of protein to polysaccharide is not optimal. For example, the isoelectric point of casein is about 4.6. If the complexation reaction of casein with agar is conducted at pH 3.7, an M-complex (i.e. a water insoluble precipitate) is formed when the ratios of protein to polysaccharide are not optimized. Thus, it is preferred that the complexation reaction occur at a pH which is equal to or greater than the isoelectric point of the protein used to make the PPC. At this pH it may be desireable to add metal ions, such as calcium, potassium, sodium, magnesium, and the like, which will facilitate the complexation reaction. When the complexation reaction is conducted at a pH which is equal to or greater than the isoelectric point of the protein, a T-complex (also known as a water soluble or water dispersible complex) results. While optimally, a T-complex is formed at a pH which is equal to or greater than the isoelectric point of the protein used to form the PPC, after it is formed it is stable and may be incorporated into cosmetic compositions which have a pH which is substantially below the isoelectric point of the protein.

THE COMPOSITIONS

The PPC may be used in a wide variety of compositions, including foundation makeups, skin lotions and creams, sunscreens, blushes, mascaras, eyeshadows, in addition to hair care products such as shampoos, conditioners, and the like. Suggested ranges of PPC are 0.01–50%, preferably 0.05–40%, more preferably 0.1–30% by weight of the total composition. The composition into which the PPC is incorporated contains at least one surfactant, which may be an anionic, amphoteric, nonionic, cationic, or zwitterionic surfactant.

Foundation Makeup, Color Cosmetics

The PPC may be used in foundation makeup or color cosmetics such as eyeshadow, blush, concealer, or eyeliner compositions in the liquid, cream, solid, or stick form. Suitable compositions may be water-in-oil or oil-in-water emulsions, but are preferably oil-in-water emulsions. Such compositions generally comprise:

0.01–50% PPC,
0.5–95% water,
0.5–25% particulate matter,
0.01–20% surfactant, and
0.1–95% oil.

In addition, these composition may further contain ingredients selected from the group of humectants, preservatives, nonvolatile or volatile oils, gellants, and mixtures thereof.

PARTICULATE MATTER

The makeup or color cosmetic compositions preferably comprises 1–20%, more preferably 1.5–18% of particulate matter having a particle size of 0.01 to 200, preferably 0.25–100 microns. The particulate matter may be colored or non-colored (for example white) non-pigmentitious powders that may give the cosmetic stick an opaque or semi-opaque quality and contribute to stick structure. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. While titanium dioxide is commonly considered to be a white pigment when used in paints, in cosmetic sticks it is used more for its ability to mute color, and/or provide an opaque or semi-opaque finish, then as a colorizing ingredient. The above mentioned powders may be surface treated with lecithin, amino acids, mineral oil, silicone, or various other agents either alone or in combination, which coat the powder surface and render the particles more lipophilic in nature.

The particulate matter component also may comprise various organic and/or inorganic pigments, alone or in admixture with one or more non-pigmentatious powders. The organic pigments are generally various aromatic types including azo, indigoid, triphenylmethane. anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The composition may contain a mixture of both pigmentatious and non-pigmentatious particulate matter. The percentage of pigment used in the particulate matter component will depend on the type of cosmetic being formulated.

SURFACTANT

The makeup or color cosmetic compositions of the invention preferably comprise 0.05–18%, more preferably 0.1–15% by weight of a surfactant. The surfactant is preferably nonionic. Suitable nonionic emulsifiers include alkoxylated alcohols, or ethers, formed by the reaction of an with an alkylene oxide, usually ethylene or propylene oxide. Preferably the alcohol is either a fatty alcohol having 6 to 30 carbon atoms. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Preferred are alkoxylated alcohols which are formed by the reaction of stearic acid, methyl glucose, and and ethoxylated alcohol, otherwise known as PEG-20 methyl glucose sesquiisostearate.

Also suitable as the nonionic surfactant are alkyoxylated carboxylic acids, which are formed by the reaction of a carboxylic acid with an alkylene oxide or with a polymeric ether. The resulting products have the general formula:

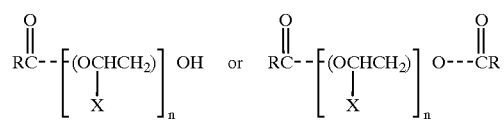

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

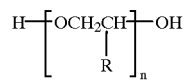

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w / M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxypolypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof.

The term "lipophilic radical" means an organic radical that, when substituted onto the organosiloxane polymer backbone, confers lipophilic properties to the substituted portion of the polymer. Examples of organic radicals which will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane surfactant used in the invention may have any of the following general formulas:

$$M_xQ_y, \text{ or}$$

$$M_xT_y, \text{ or}$$

$$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical.

Preferred is a linear silicone of the formula:

$$MD_xD'_yD''_zM$$

wherein M=$RRRSiO_{1/2}$
D and D'=$RR'SiO_{2/2}$
D''=$RRSiO_{2/2}$
x, y, and z are each independently 0–1000,
where R is methyl or hydrogen, and R' is a hydrophilic radical or a lipophilic radical, with the proviso that the compound contains at least one hydrophilic radical and at least one lipophilic radical.

Most preferred is wherein
M=trimethylsiloxy
D=$Si[(CH_3)][(CH_2)_nCH_3]O_{2/2}$ where n=0–40,
D'=$Si[(CH_3)][(CH_2)_o$—O—PE)]$O_{2/2}$ where PE is $(-C_2H_4O)_a(-C_3H_6O)_bH$, o=0–40,
a=1–100 and b=1–100, and
D''=$Si(CH_3)_2O_{2/2}$ More specifically, suitable silicone surfactants have the formula:

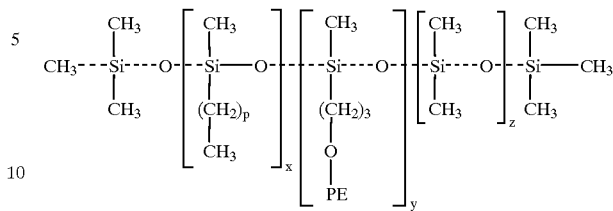

wherein p is 0–40, preferably 12–20, most preferably 15, and

PE is $(-C_2H_4O)_a(-C_3H_6O)_b$—H where x, y, z, a, and b are such that the maximum molecular weight of the polymer is approximately 50,000.

Another type of preferred organosiloxane emulsifier suitable for use in the compositions of the invention are emulsifiers sold by Union Carbide under the SILWET™ trademark. These emulsifiers are represented by the following generic formulas:

wherein PE=—$(EO)_m(PO)_nR$
R=lower alkyl or hydrogen
Me=methyl
EO is polyethyleneoxy
PO is polypropyleneoxy
m and n are each independently 1–5000
x and y are each independently 0–5000, and

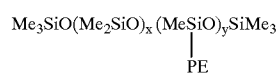

wherein PE=—$CH_2CH_2CH_2O(EO)_m(PO)_nZ$
Z=lower alkyl or hydrogen, and
Me, m, n, x, y, EO and PO are as described above,
with the proviso that the molecule contains a lipophilic portion and a hydrophilic portion. Again, the lipophilic portion can be supplied by a sufficient number of methyl groups on the polymer.

Also suitable as nonionic silicone surfactants are hydroxy-substituted silicones such as dimethiconol, which is defined as a dimethyl silicone substituted with terminal hydroxy groups.

Examples of silicone surfactants are those sold by Dow Corning under the tradename Dow Corning 3225C Formulation Aid, Dow Corning 190 Surfactant, Dow Corning 193 Surfactant, Dow Corning Q2-5200, and the like are also suitable. In addition, surfactants sold under the tradename SILWET by Union Carbide, and surfactants sold by Troy Corporation under the TROYSOL tradename, those sold by Taiwan Surfactant Co. under the tradename ABLUSOFT, those sold by Hoechst under the tradename ARKOPHOB, are also suitable for use in the invention.

In the preferred compositions of the invention, the nonionic surfactant is selected from an alkoxylated alcohol, or ether, formed by the reaction of a fatty acid with a polyhydric alcohol such as glucose or methyl glucose and an ethoxylated alcohol; a sorbitan derivative, and mixtures thereof. Particularly preferred is a nonionic surfactant selected from polyoxyethylene 3-oleyl ether, Polysorbate 20, sorbitan stearate, PEG-20 methyl glucose sesquiisostearate, and mixtures thereof.

Suitable cationic, anionic, zwitterionic, and amphoteric surfactants are disclosed in U.S. Pat. No. 5,534,265, which ishereby incorporated by reference in its entirety.

HUMECTANT

Preferably the makeup or color cosmetic compositions of the invention comprise 0.1–30%, preferably 0.5–25%, more preferably 1–20% by weight of the total composition of humectant. Suitable humectants include materials glycols, sugars, and similar materials. Suitable glycols include polyethylene and polypropylene glycols such as PEG 4–240, which are polyethylene glycols having from 4 to 240 repeating ethylene oxide units; as well as $C_{1-6}$ alkylene glycols such as propylene glycol, butylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Preferably, the humectants used in the composition of the invention are $C_{1-6}$, preferably $C_{2-4}$ alkylene glycols, most particularly butylene glycol.

GELLANTS

It may be desireable to include other gellants in the oil or water phase of the composition to provide optimal gelling properties or, if desired, to formulate the makeup composition in the form of a solid stick. Other gellants may be included a range of 1–20%, preferably 3–18%, more preferably 5–10% by weight of the total compositions is suggested. Suitable gellants include soaps, i.e. salts of water insoluble fatty acids with various bases. Examples of soaps include the aluminum, calcium, magnesium, potassium, sodium, or zinc salts of $C_{6-30}$, preferably $C_{10-22}$ fatty acids.

Examples of such ingredients include aluminum, calcium, magnesium, potassium, sodium, or zinc stearate, isostearate, laurate, linoleate, myristate, oleate, olivate, palmate, palmitate, tallowate, rosinate, and the like. Particularly preferred gellants are sodium salts of $C_{2-18}$ fatty acids, in particular sodium stearate, sodium isostearate, and the like.

OILS

It may be desireable to include one or more additional oils in the makeup compositions of the invention. If so, a range of 0.1–50%, preferably 0.5–40%, more preferably 1–35% by weight of the total composition is suggested. The oils used may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. If the cosmetic compositions of the invention are transfer resistant sticks, it is desireable to use significant amounts of volatile solvent for the oil component. Suitable volatile solvents or oils are liquids, and enable easy formulation of the cosmetic stick of the invention. When the cosmetic stick product of the invention is applied to skin or lips, the volatile solvent of the invention must be capable of flashing off to leave the other ingredients in the stick on the skin. Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) are of the general formula:

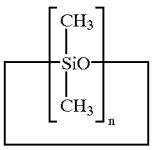

where n=3–7.

Linear volatile silicones in accordance with the invention have the general formula:

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated bv reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename PERMETHYL 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A. Cosmetic Ingredient Handbook*, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleale, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Straight or branched chain fatty alcohols having the formula R—OH, wherein R is a straight or branched chain saturated or unsaturated alkyl having 6–30 carbon atoms, are also suitable oils. Such fatty alcohols include cetyl alcohol, stearyl alcohol, cetearyl alcohol, and the like.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C. Suitable water insoluble silicones include amodimethicone, bisphenylhexametlticone, dimethicone, hexadecyl methicone, methicone, phenyl trimethicone, simethicone, dimethylhydrogensiloxane, stearoxytrimethylsilane, vinyldimethicone, and mixtures thereof. Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

Also suitable as the nonvolatile oil are various fluorinated oils such as fluorinated silicones. fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

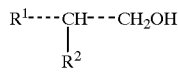

with a carboxylic acid having the general formula:

R³COOH, or

HOOC—R³—COOH wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonyihydroxy. Particularly preferred is a carboxylic acid wherein the R group is such to provide an ingredient known as meadowfoam seed oil.

Preferably, the guerbet ester is a fluoro-guerbet ester which is formed by the reaction of a guerbet alcohol and carboxylic acid (as defined above), and a fluoroalcohol having the following general formula:

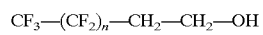

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Georgia as Developmental Ester L61125A, under the tradename Silube GMEF.

Preferably, the compositions of the invention are makeup compositions, and contain a water insoluble nonvolatile silicone having a viscosity of about 5–25 centipoise at 25° C., which is preferably dimethicone.

PRESERVATIVES

The composition may contain 0.001–8%, preferably 0.01–6%, more preferably 0.05–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, captan, chlorhexidine diacetate, chlorhexidine digluconate, chlorhexidine dihydrochloride, chloroacetarnide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

Lotions, Creams, Gels, and Sunscreens

The PPC may be used to make skin care products such as lotions, creams, gels, and sunscreens.

Suitable skin care lotions and creams are in the emulsion form, and may be water-in-oil or oil-in-water emulsions, preferably oil-in-water emulsions. Creams, lotions, and/or may contain the following ranges of ingredients:

0.01–50% PPC, 0.5–95% water, 0.1–50% oil, and 0.01–20% surfactant.

Suitable oils and surfactants are as mentioned herein.

SKIN TREATING ACTIVE INGREDIENTS

In addition, these compositions may contain one or more skin-treating active ingredients in ranges of about 0.1–15%, preferably 0.5–10%, more preferably 1–8% by weight of the total composition. Particularly preferred skin treating active agents are acidic keratolytic or anti-acne agents such as alpha or beta hydroxy acids and/or alpha keto acids. Suitable alpha hydroxy acids and alpha ketoacids are disclosed in U.S. Pat. No. 5,091,171, which is hereby incorporated by reference. Such alpha hydroxy acids are as follows:

a) Organic carboxylic acids where one hydroxyl group is attached to the alpha carbon atom of the acid. The general structure of such alpha hydroxy acids may be represented by the following formula:

(Ra)(Rb)C(OH)COOH wherein Ra and Rb are H, F, Cl, Br, alkyl, aralkyl, or aryl group of saturated, unsaturated, straight or branched chain or cyclic form having 1–10 carbon atoms, and in addition Ra or Rb may carry OH, CHO, COOH and alkoxy groups having 1 to 9 carbon atoms.

The second group of alpha hydroxy acids may be represented by the following formula:

(Ra)CO COO(Rb)

wherein Ra and Rb are H, alkyl, aralkyl, or aryl groups of straight or branched chain saturated or unsaturated alkyl having 1 to 10 carbon atoms, and in addition Ra may carry F, Cl, Br, I, OH, CHO, COOH, and alkoxy groups having 1 to 10 carbon atoms.

The alpha hydroxy acids may exist in the keto acid form, or the ester form. Examples of such alpha hydroxy acids include glycolic acid, malic acid, pyruvic acid, mandelic acid, lactic acid, methyllactic acid, and so on.

Also beta hydroxy acids such as salicylic acid, and derivatives thereof may be included in the compositions of the invention. Particularly preferred are skin care compositions which contain one or more alpha or beta hydroxy acids, which compositions have a pH of 2 to about 4.5. A particularly preferred skin treating active agent is salicylic acid complexed with a complexing agent having at least one free amino or hydroxy group as disclosed in U.S. Pat. No. 5,449,519, which is hereby incorporated by reference, and the like. Particularly preferred is salicylic acid complexed to hydrolyzed vegetable protein in about a 50:50 ratio. When such acidic skin-treating active agents are used in skin care compositions, the pH of the compositions is generally in the acidic range, which may be below the isoelectric point of the protein which is used to make the PPC. As previously noted, if the PPC is made at a pH which is at or above the isoelectric point of the protein, a T-complex will be formed, which is stable when subsequently formulated into skin care compositions which have a pH which is below the isoelectric point of the protein used to make the PPC.

SUNSCREENS

The compositions of the invention may contain 0.001–20%, preferably 0.01–10%, more preferably 0.05–8% of one or more sunscreens. A sunscreen is defined as an ingredient that absorbs at least 85 percent of the light in the UV range at wavelengths from 290 to 320 nanometers, but transmit UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the *CTFA Cosmetic Ingredient Handbook*, Second Edition, 1992, as well as U.S. Pat. No. 5,620,965, both of which are hereby incorpated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)]amnobenzoate (ethyl dihydroxypropyl PABA), 2-ethylhexyl-2-cyano-3,3-diphenylacrylate (octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), Padimate O, (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), and so on.

VITAMINS AND ANTIOXIDANTS

The compositions of the invention may contain vitamins and/or coenzymes, as well as antioxidants. If so, 0.001–10%, preferably 0.01–8%, more preferably 0.05–5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

In addition, the skin care lotions, creams, gels, and sunscreens may have the ranges of nonvolatile oil, humectant, particulate matter, and preservatives, and other ingredients mentioned with respect to the makeup compositions.

Skin and Hair Cleansing and Conditioning Compositions

The PPC may be incorporated into skin and hair cleansing and conditioning compositions such as facial cleansers, shampoos, hair conditioners and the like.

Generally skin and hair cleansing compositions comprise:
1–95% water, and
0.1–40% surfactant, preferably an anionic, amphoteric, or zwitterionic surfactant.

Particularly preferred is a facial cleanser comprising:
0.05–10% PPC,
0.01–40% surfactant,
and the remainder water. Preferably the surfactant is a nonionic or anionic surfactant, or mixtures thereof, as mentioned herein.

Suitable hair conditioner compositions comprise:
0.1–20% cationic surfactant,
0.1–30% fatty alcohol,
0.001–10% nonionic surfactant, and
5–95% water.

Suitable cationic and nonionic surfactants are as mentioned herein. Examples of suitable fatty alcohols include those having the general formula R—OH, wherein R is a $C_{6-30}$ straight or branched chain, saturated or unsaturated alkyl.

The invention will be further described in connection with the following examples which are set forth for the purposes of illustration only.

EXAMPLE 1

PPC's were made as follows using cosmetic grade casein, CG101, purchased from American Casein Co. as the protein. For the polysaccharides, iota and kappa carageenen purchased from FMC Corporation, and agarose purchased from Sigma Chemical Company was used. The protein and polysaccharides were dissolved in water at 65° C., as set forth below, with the pH being adjust with HCl or KOH as appropriate after the PPC was formed. In the mixtures designed A', the pH was adjusted before the protein was mixed with the polysaccharide.

| Solution | Composition |
|---|---|
| A | 1.67 g. casein + 306.5 g. water, pH = 7 |
| B | 1.81 g. iota carageenan + 349.5 g. water, pH = 6 |
| C | 1.70 g. kappa carageenen + 312.16 g. water, pH = 6 |
| D | 2.01 g. agarose + 383.48 g. water, pH = 6 |
| E | 10% aqueous solution of $CaCl_2$ |

Mixtures were made using the following amounts of components A, B, C, D, and E:

A: 20 g. B: 20 g. C: 20 g. D: 20 g. E: 19 g.

| Mixture | pH | Appearance |
|---|---|---|
| A + B + E | 4.50 | gelled blue dispersion; T-complex formed |
| A + B | 3.72 | gelled blue dispersion, T-complex formed |
| A + B | 4.50 | gelled blue dispersion, T-complex formed |
| A' + B | 3.75 | liquid with white, fine precipitate, M-complex formed |
| A | 4.5 | white course precipitate |
| ½B + A | 4.5 | transparent gel, T-complex formed |
| A + C + E | 4.50 | liquid, blue dispersion, T-complex formed |
| A + C | 4.50 | liquid blue dispersion, T-complex formed |
| A + C | 3.50 | liquid with fine white precipitate, M-complex formed by acidifying A to pH 3 before mixing |
| A + C | 3.50 | liquid, blue dispersion, T-complex formed |
| A + C | 6.97 | transparent blue dispersion, T-complex formed |
| A + D + E | 3.7 | blue dispersion, weak gel |
| A + D | 3.7 | blue dispersion, weak gel |
| A + D | 4.5 | blue dispersion, weak gel |
| A' + D | 3.7 | liquid with white, fine precipitate. |

EXAMPLE 2

A PPC was made by mixing 0.2 grams of casein was mixed into 99 grams of water having a temperature of 25° C. with stirring. After the casein was completely dissolved the solution was adjusted to pH 9 with concentrated sodium hydroxide. Then 0.8 grams of iota carageenan were added and the mixture was heated to 70° C. with stirring until a clear solution was obtained. At 70° C. the solution was in liquid form. When cooled to 36° C. the solution formed a gel.

EXAMPLE 3

The PPC made in Example 2 was used to prepare the following compositions: (1) an oil-in-water brush on foundation make-up (2) an oil-in-water eyeshadow, (3) an oil-in-water eyeliner, as follows:

| | w/w % | | |
|---|---|---|---|
| | (1) | (2) | (3) |
| A | | | |
| Coco-caprylate/caprate | 10.00 | 10.00 | 10.00 |
| Cyclomethicone | 10.00 | 10.00 | 10.00 |
| Dimethicone (10 centipoise) | 1.00 | 1.00 | 1.00 |
| B | | | |
| Polyoxyethylene(3)oleyl ether | 1.50 | 1.50 | 1.50 |
| Polyoxyethylene 20 sorbitan monolaurate | 0.50 | 0.50 | 0.50 |
| C | | | |
| Milk protein arginate | 1.00 | 2.00 | 2.00 |
| Butylene glycol | 14.00 | 14.00 | 14.00 |
| Methyl paraben | 0.20 | 0.20 | 0.20 |
| Propyl paraben | 0.10 | 0.10 | 0.10 |
| D | | | |
| Red No. 6* | 2.00 | — | — |
| Yellow iron oxide | — | 3.00 | 0.40 |
| Silicone treated mica | — | 3.00 | — |
| Black iron oxide | — | — | 2.00 |
| Water | 59.70 | 58.70 | 60.30 |

EXAMPLE 4

The PPC made in Example 2 was used to prepare oil-in-water emulsion creams (1) and (3) and gels (2) and (4), as follows:

| | w/w % | | | |
|---|---|---|---|---|
| | 1 | 2 | 3 | 4 |
| A | | | | |
| Coco-caprylate/caprate | 20.00 | 20.00 | — | — |
| Cyclomethicone | — | — | 20.00 | — |
| Dimethicone | — | — | — | 20.00 |
| B | | | | |
| Polyoxyethylene (3) oleyl ether | 1.50 | — | — | — |
| Sorbitan stearate | — | 1.50 | 1.50 | 1.50 |
| Polyoxyethylene 20 sorbitan monolaurate | 0.50 | 4.50 | 4.50 | 4.50 |
| Milk protein arginate | 0.20 | 1.00 | 0.20 | 1.00 |
| Butylene glycol | 14.00 | 14.00 | 14.00 | 14.00 |
| Methyl paraben | 0.20 | 0.20 | 0.20 | 0.20 |
| Propyl paraben | 0.10 | 0.10 | 0.10 | 0.10 |
| C | | | | |
| Salicylic acid | — | — | 2.00 | — |
| Ethanol | — | — | 5.00 | — |
| Titanium dioxide | 1.00 | 1.00 | 1.00 | 1.00 |
| Water | 62.50 | 77.70 | 51.50 | 57.7 |

EXAMPLE 5

Oil-in-water sunscreen compositions in the cream (1) and (3), and gel (2), (4), and (5) form were made using the PPC made in Example 2, according to the following formulas:

|  | w/w % | | | | |
| --- | --- | --- | --- | --- | --- |
|  | 1 | 2 | 3 | 4 | 5 |
| A | | | | | |
| Coco-caprylate/caprate | 20.00 | 20.00 | — | — | — |
| Cyclomethicone | — | — | 20.00 | — | — |
| Dimethicone | — | — | — | 20.00 | 20.00 |
| B | | | | | |
| Polyoxyethylene(3) oleyl ether | 1.50 | — | — | — | — |
| PPC | 0.20 | 1.00 | 1.00 | 1.00 | 1.00 |
| Microcrystalline cellulose | — | 1.00 | 1.00 | 1.00 | 1.00 |
| Butylene glycol | 14.00 | 14.00 | 14.00 | 14.00 | 14.00 |
| Methyl paraben | 0.20 | 0.20 | 0.20 | 0.20 | 0.20 |
| Propyl paraben | 0.10 | 0.10 | 0.10 | 0.10 | 0.10 |
| C | | | | | |
| Titanium dioxide | 8.00 | 8.00 | 8.00 | 8.00 | 8.00 |
| Zinc oxide | — | — | — | — | 8.00 |
| Water | 55.50 | 69.70 | 50.50 | 49.70 | 57.70 |

EXAMPLE 7

Oil-in-water foundation stick makeups were made using the PPC made in Example 2, according to the following formulas:

|  | w/w % | | | | |
| --- | --- | --- | --- | --- | --- |
|  | 1 | 2 | 3 | 4 | 5 |
| A | | | | | |
| Coco-caprylate/caprate | 20.00 | 20.00 | 20.00 | — | — |
| Cyclomethicone | — | — | — | 20.00 | — |
| Dimethicone | — | — | — | — | 20.00 |
| B | | | | | |
| Polyoxyethylene 3 oleyl ether | 1.50 | 1.50 | — | — | — |
| Sorbitan stearate | — | — | 1.50 | 1.50 | 1.50 |
| Polyoxyethylene 20 sorbitan monolaurate | 0.50 | 0.50 | 4.50 | 4.50 | 4.50 |
| Microcrystalline cellulose | — | 1.00 | — | — | — |
| PPC | — | 1.00 | 1.00 | 1.00 | 1.00 |
| C | | | | | |
| Butylene glycol | 14.00 | 14.00 | 14.00 | 14.00 | 14.00 |
| Methyl paraben | 0.20 | 0.20 | 0.20 | 0.20 | 0.20 |
| Propyl paraben | 0.10 | 0.10 | 0.10 | 0.10 | 0.10 |
| Red iron oxide | 1.40 | 1.40 | 1.40 | 1.40 | 1.40 |
| Yellow iron oxide | 1.40 | 1.40 | 1.40 | 1.40 | 1.40 |
| Black iron oxide | 0.17 | 0.17 | 0.17 | 0.17 | 0.17 |
| Titanium dioxide | 8.00 | 8.00 | 8.00 | 8.00 | 8.00 |
| Water | 51.73 | 50.23 | 66.73 | 46.73 | 46.73 |

EXAMPLE 8

An oil-in-water emulsion makeup stick was made according to the following formula, using the PPC made in Example 2.

|  | w/w % |
| --- | --- |
| A | |
| Sodium stearate | 7.56 |
| Water | 43.77 |
| Phenoxyethanol | 0.50 |
| Propyl paraben | 0.10 |
| Methyl paraben | 0.30 |
| Butylene glycol | 13.04 |
| Calcium chloride | 0.80 |
| PPC | 0.80 |
| PEG-20 methyl glucose sesquiisostearate | 3.49 |
| B | |
| Hydrogenated castor oil | 2.00 |
| Isostearyl alcohol | 5.74 |
| Titanium dioxide | 0.74 |
| Iron oxide yellow | 1.05 |
| Iron oxide red | 0.33 |
| Iron oxide black | 0.13 |
| Talc | 2.23 |
| Dimethicone | 11.63 |
| Titanium dioxide/trimethylolethane | 6.30 |

The makeup compositions were made by mixing all ingredients in phase B together and grinding the ingredients for 30 minutes. The phase A ingredients were slowly added to the phase B ingredients with constant mixing. The C ingredients were then added with mixing.

EXAMPLE 9

A skin lotion was made according to the following formula:

|  | w/w % |
| --- | --- |
| PPC | 1.60 |
| Trisodium EDTA | 0.10 |
| Butylene glycol | 5.00 |
| Sorbitan stearate/sucrose cocoate | 6.00 |
| Methyl paraben | 0.25 |
| Ethyl paraben | 0.15 |
| Xanthan gum | 0.30 |
| Octyl methoxycinnamate | 7.50 |
| Octyl salicylate | 5.00 |
| Benzophenone-3 | 3.00 |
| C12-15 alkyl benzoate | 8.00 |
| Cetyl alcohol | 1.00 |
| Phenoxyethanol | 1.00 |
| Propyl paraben | 0.10 |
| Water | QS |

EXAMPLE 10

A foaming skin cleanser was made according to the following formula:

|  | w/w % |
| --- | --- |
| PPC* | 0.200 |
| Butylene glycol | 5.00 |
| Isoceteth-20/water (72:28) | 3.00 |
| Tocopheryl acetate | 0.100 |
| Retinyl palmitate | 0.010 |
| Trisodium EDTA | 0.050 |
| Magnesium ascorbyl phosphate | 0.100 |

-continued

| | w/w % |
|---|---|
| Methoxypropylgluconamide | 0.160 |
| Salicylic acid/hydrolyzed vegetable protein (50:50) | 0.500 |
| Hydrolyzed soy flour | 0.500 |
| Methyl paraben | 0.200 |
| Propyl paraben | 0.050 |
| Triclosan | 0.500 |
| Menthol | 0.200 |
| TEA N-acyl-L-glutamate | 16.600 |
| Water | QS |

The composition was made by combining the ingredients and mixing well.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. In a water and silicone oil emulsion cosmetic composition for application to skin or hair containing water and at least one surfactant, the improvement wherein the composition also contains 0.1–50% by weight of the total composition of a water soluble, protein polysaccharide complex ("PPC") having a net negative charge, which is the reaction product of a protein selected from the group consisting of casein, milk protein, hydrolyzed vegetable protein, and mixtures thereof; and a polysaccharide having pendant hydrophilic groups containing sulfate moieties selected from the group consisting of galactan, galactonmannan, glucomannan and mixtures thereof; and a metallic ion selected from the group consisting of calcium, potassium, sodium, magnesium, according to the following reactions I or II below:

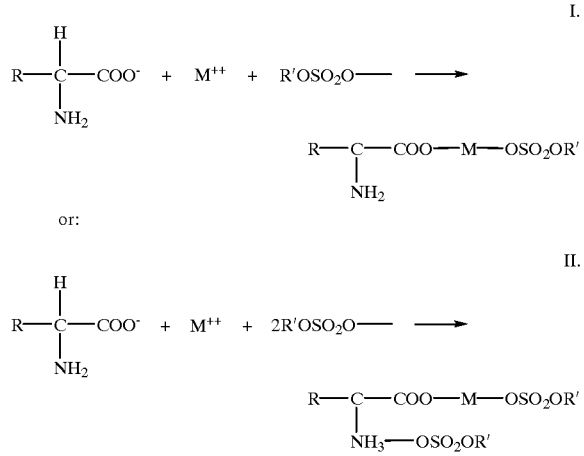

wherein:

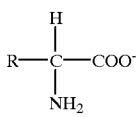

represents the protein; R'OSO$_2$O— represents the polysaccharide; and M++ represents the metallic ion; said reaction conducted at a pH above the isoelectric point of the protein and wherein the ratio of protein to polysaccharide in the complex is 1:50 to 50:1 respectively.

2. The composition of claim 1 wherein the protein is water soluble or water dispersible.

3. The composition of claim 2 wherein the protein is casein or milk protein.

4. The composition of claim 3 wherein the protein is casein.

5. The composition of claim 3 wherein the protein is milk protein.

6. The composition of claim 1 wherein the polysaccharide has a molecular weight ranging from about 500 to 15,000,000 daltons.

7. The composition of claim 6 wherein the polysaccharide is a galactan.

8. The composition of claim 7 wherein the polysaccharide is agar, agarose, carageenan, or mixtures thereof.

9. The composition of claim 8 wherein the polysaccharide is selected from agar, carageenan, and mixtures thereof.

10. The composition of claim 1 wherein the cosmetic composition is a makeup comprising, by weight of the total composition:

0.01–50% of the protein/polysaccharide complex ("PPC") where the protein is selected from the group consisting of casein and milk protein, and the polysaccharide is a galactan selected from the group consisting of agar and carrageenan, 0.5–95% water, 0.5–25% particulate matter, and 0.01–20% of a nonionic surfactant.

11. The composition of claim 10 wherein the protein is milk protein.

12. The composition of claim 11 wherein the galactan is carageenan.

13. The composition of claim 10 additionally comprising 0.1–30% by weight of the total composition of humectant.

14. The composition of claim 10 additionally comprising 1–20% by weight of the total composition of a gellant.

15. The composition of claim 14 wherein the gellant is a soap.

16. The composition of claim 15 wherein the soap is salt of a fatty acid.

17. The composition of claim 1 which is a skin cream or lotion additionally comprising a skin-treating active agent.

* * * * *